United States Patent
Parthasarathy

(10) Patent No.: US 9,464,999 B2
(45) Date of Patent: Oct. 11, 2016

(54) DETECTING TEMPERATURE SENSOR ANOMALIES

(71) Applicant: Honeywell International Inc., Morristown, NJ (US)

(72) Inventor: Girija Parthasarathy, Maple Grove, MN (US)

(73) Assignee: Honeywell International Inc., Morris Plains, NJ (US)

( * ) Notice: Subject to any disclaimer, the term of this patent is extended or adjusted under 35 U.S.C. 154(b) by 467 days.

(21) Appl. No.: 14/071,556

(22) Filed: Nov. 4, 2013

(65) Prior Publication Data

US 2015/0124850 A1    May 7, 2015

(51) Int. Cl.
| | | |
|---|---|---|
| *G01K 7/00* | (2006.01) | |
| *G01R 31/00* | (2006.01) | |
| *G08C 19/00* | (2006.01) | |
| *G01N 25/72* | (2006.01) | |
| *G01K 1/00* | (2006.01) | |
| *F24F 11/00* | (2006.01) | |

(52) U.S. Cl.
CPC ........... *G01N 25/72* (2013.01); *F24F 11/0012* (2013.01); *G01K 1/00* (2013.01); *F24F 2011/0016* (2013.01); *F24F 2011/0052* (2013.01)

(58) Field of Classification Search
CPC .............................. G01N 25/00; G01N 25/72
USPC ...... 702/99, 130; 714/100, 102; 340/870.17; 324/500, 511, 512; 236/91 R, 91 D, 236/91 G, 91 F, DIG. 8, DIG. 14
See application file for complete search history.

(56) References Cited

U.S. PATENT DOCUMENTS

| | | | | |
|---|---|---|---|---|
| 3,610,894 A | * | 10/1971 | Drury ................... | H03K 5/153 235/62 R |
| 5,317,908 A | * | 6/1994 | Fitzgerald ............ | G01N 11/162 73/54.25 |
| 5,637,814 A | * | 6/1997 | Timmons ................. | G01K 1/14 374/E1.018 |
| 6,179,785 B1 | * | 1/2001 | Martinosky ............... | G01J 5/02 374/E13.003 |
| 6,401,018 B1 | * | 6/2002 | Oba .................... | G01R 31/2829 327/20 |
| 6,513,723 B1 | * | 2/2003 | Mueller .................. | F23N 5/143 236/46 R |
| 6,670,888 B2 | * | 12/2003 | Schmidt ................. | B60R 21/01 340/647 |
| 6,804,600 B1 | | 10/2004 | Uluyol et al. | |
| 8,204,672 B2 | | 6/2012 | Mylaraswamy et al. | |
| 2003/0016124 A1 | * | 1/2003 | Schmidt ................. | B60R 21/01 340/425.5 |

(Continued)

*Primary Examiner* — Gail Kaplan Verbitsky
(74) *Attorney, Agent, or Firm* — Schwegman Lundberg & Woessner, P.A.

(57) ABSTRACT

Generally discussed herein are techniques, software, apparatuses, and systems configured for detecting an anomaly in a temperature sensor. In one or more embodiments an apparatus can include one or more computer processors configured to: (1) receive a series of temperature sensor readings from a temperature sensor, (2) determine if the temperature sensor is exhibiting behavior consistent with experiencing oscillations as a function of the received sensor readings, and (3) in response to determining that the temperature sensor is exhibiting behavior consistent with experiencing oscillations, recording in a memory data indicating that the temperature sensor is exhibiting behavior consistent with experiencing oscillations.

5 Claims, 12 Drawing Sheets

(56) References Cited

U.S. PATENT DOCUMENTS

| | | | | |
|---|---|---|---|---|
| 2010/0088061 A1* | 4/2010 | Horodezky | ............ | G06F 1/1624 702/141 |
| 2012/0273581 A1* | 11/2012 | Kolk | ...................... | F24F 11/006 236/91 D |
| 2012/0294327 A1* | 11/2012 | Kamata | .................... | H03B 5/04 374/1 |
| 2014/0348208 A1* | 11/2014 | Hashemian | .............. | G01K 7/18 374/179 |
| 2014/0351642 A1* | 11/2014 | Bates | .................. | G06F 11/0709 714/26 |
| 2015/0168462 A1* | 6/2015 | Singh | ................. | G01R 19/0092 702/64 |
| 2015/0241079 A1* | 8/2015 | Matsuoka | ........... | H04L 12/2825 700/276 |

* cited by examiner

DETECTING TEMPERATURE SENSOR ANOMALIES

BACKGROUND

Thermostats are commonly used to help control temperature, humidity, and other comfort level factors in individual structures and zones within those structures. The number of thermostats used in the United States is increasing. The thermostats can be coupled to temperature and humidity sensors and can be coupled to the internet. The thermostat can be programmed to trigger a heating and cooling system to either heat or cool a zone when the temperature or humidity goes above or below a programmed threshold.

SUMMARY

An apparatus can include one or more computer processors configured to: (1) receive a series of temperature sensor readings from a temperature sensor, (2) determine if the temperature sensor is exhibiting behavior consistent with experiencing oscillations as a function of the received sensor readings, and (3) in response to determining that the temperature sensor is exhibiting behavior consistent with experiencing oscillations, recording in a memory data indicating that the temperature sensor is exhibiting behavior consistent with experiencing oscillations.

A technique can include receiving a series of temperature sensor readings from a temperature sensor, determining if the temperature sensor is exhibiting behavior consistent with experiencing oscillations as a function of the received sensor readings, and in response to determining that the temperature sensor is exhibiting behavior consistent with experiencing oscillations, recording in a memory data indicating that the temperature sensor is exhibiting behavior consistent with experiencing oscillations.

A computer readable storage device can include instructions stored thereon, the instructions, which when executed by a machine, cause the machine to perform operations including receiving a series of temperature sensor readings from a temperature sensor, determining if the temperature sensor is exhibiting behavior consistent with experiencing oscillations as a function of the received sensor readings, and in response to determining that the temperature sensor is exhibiting behavior consistent with experiencing oscillations, recording in a memory data indicating that the temperature sensor is exhibiting behavior consistent with experiencing oscillations.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
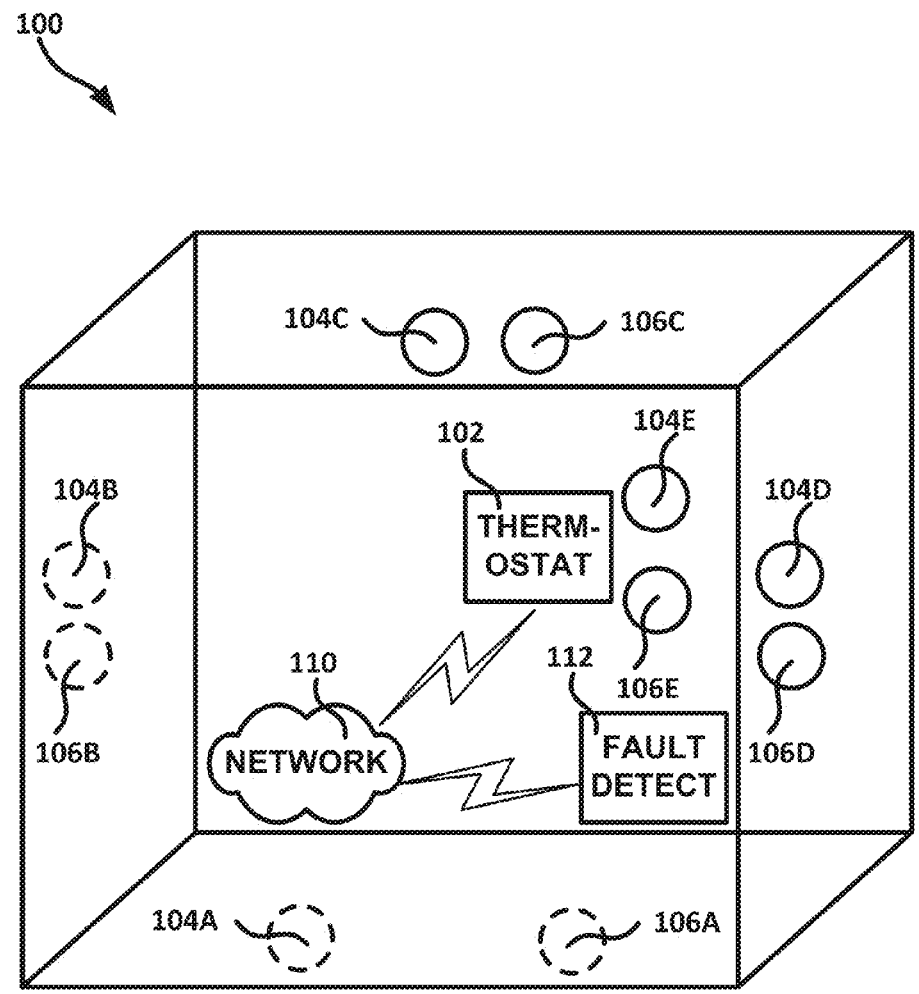
FIG. 1 illustrates a block diagram of an example of a comfort level system in an area (e.g., room(s), building(s), zone(s), other area, or a combination thereof).

While embodiments of this disclosure can take many different forms, specific embodiments thereof are shown in the drawings and will be described herein in detail with the understanding that the present disclosure is to be considered as an exemplification of the principles of the invention, as well as the best mode of practicing same, and is not intended to limit the disclosure to the specific embodiments illustrated.

Connected thermostats can create large amounts of data. Analytics on the data created by these thermostats can have the potential to provide insights for smart grid and utility businesses. The insight can be in the form of a forecast of demand response potential, operational set point recommendations for energy or cost savings, energy efficiency upgrade recommendations, or diagnosis of equipment problems, among others. Connected thermostats (e.g., thermostats connected to the internet) can produce time-series data including an indoor display temperature and humidity, temperature set points, outdoor temperature and humidity, or heating or cooling mode. The data can be recorded when a change in the data occurs or periodically regardless of whether the data value has changed.

An outdoor temperature sensor for a thermostat can be either not installed correctly or located incorrectly (e.g., not outdoors). Sometimes the temperature sensor can produce high frequency oscillatory data, such as around a mean value, such as a mean value not related to (e.g., with little or no correlation to) the actual outdoor temperature. These anomalies can be detected, such as to allow corrective action to be taken. Algorithms configured to detect, such as automatically (e.g., without human action or interference), anomalies can be helpful for additional analytics in processing thermostat data. Such algorithms can be helpful for repairing a problem or saving energy, such as to help increase customer comfort or economy.

The following description describes systems, apparatuses, techniques, and software configured to detect anomalies in a temperature sensor, such as a temperature sensor that is supposed to be located outdoors, a temperature sensor is exhibiting behavior consistent with experiencing oscillations, or that the temperature sensor is not operating properly. Such anomalies can be detected by analyzing temperature sensor readings. As used herein, as "temperature sensor reading" is data corresponding to a temperature detected at a temperature sensor.

Apparatuses, systems, techniques, and software will now be further described with references to figures.

Referring now to FIG. 1, a comfort level system 100 for an area (e.g., room, building, or other indoor space) can include one or more thermostats 102, one or more temperature sensors 104A, 104B, 104C, 104D, and 104E, or one or more humidity sensors 106A, 106B, 106C, 106D, and 106E. Humidity and temperature sensing may be implemented in a same package. For example temperature sensor 104A and humidity sensor 106A may be implemented in a single package. The following discussion regards detecting anomalies in temperature sensors, however, the same apparatuses, systems, techniques, and software can be applied to a humidity sensor to detect an anomaly in a humidity sensor.

The thermostat 102 may be wired or wirelessly coupled to the temperature sensors 104A-E or humidity sensors 106A-E. The thermostat 102 can receive air temperature information (e.g., data representative of a temperature of air) directly from the temperature sensors 104A-E or from a network 110 which the temperature sensors 104A-E are communicatively coupled to. Similarly, the thermostat 102 can receive air humidity information (e.g., data representative of a humidity of air) directly from the humidity sensors 106A-E or from a network 110 that the humidity sensors 106A-E are communicatively coupled to.

The thermostat 102 can include one or more temperature set points that can be set by a user. The one or more temperature set points can be set on a schedule. For example, a user can decide that they would like an area to be warmer during the day than at night. In such a situation, the user can set a first temperature set point for 7:00 AM and a second, different temperature set point for 11:00 PM. The thermostat 102 can use the first temperature set point as the desired temperature of the area from 7:00 AM to 11:00 PM and the second temperature set point as the desired temperature for the area from 11:00 PM to 7:00 AM. Temperature set points could be set for longer or shorter lengths of time, such as hourly, daily, weekly, monthly, etc. Temperature set points can be set based on solar activity, such as sunrise, sunset, or how much sun exposure the area is exposed to (e.g., mostly sunny, partly cloudy, etc.), among others. Information about solar activity can be retrieved through the network 110.

The thermostat 102 can include a global positioning system (GPS) sensor that it can use to determine (e.g., automatically determine) its location. The location can be used to determine weather data, such as through the internet. The thermostat 102 can use Internet Protocol (IP) address information, cell tower information, GPS, or any other wired or wireless method to determine its geographic location.

One or more air temperature sensors 104A-E can be communicatively coupled to the thermostat 102. The temperature sensors 104A-E can transmit data representative of an air temperature (e.g., a temperature reading) to the thermostat 102 either directly to the thermostat 102 or indirectly, such as through network 110. The temperature sensor 104A-E can be configured to transmit air temperature data periodically, continuously, or at or around the time the thermostat 102 requests temperature data. One or more temperature sensors 104A-E can be placed inside an area to measure inside air temperature and transmit an inside air temperature data to the thermostat 102, such as temperature sensor 104E of FIG. 1. In one or more embodiments, more than one temperature sensor 104A-E may be placed in different locations in the same area, such as an area with a large volume. One or more temperature sensors 104A-D can be placed outside an area (e.g., outdoors) to measure outside air temperature and transmit an outside air temperature reading to the thermostat 102. In the embodiment shown in FIG. 1, temperature sensors 104A-D measure outside air temperature and transmit data representative of outside air temperature to the thermostat 102.

One or more air humidity sensors 106A-E can be communicatively coupled to the thermostat 102. A humidity sensor 106A-E can transmit data representative of an air humidity to the thermostat 102, either directly to the thermostat 102 or indirectly, such as through network 110. A humidity sensor 106A-E can be configured to transmit air humidity data periodically, continuously, or at or around the time the thermostat 102 requests humidity data from the respective humidity sensor 106A-E. One or more humidity sensors 106A-E can be placed inside an area to measure inside air humidity and transmit inside air humidity data to the thermostat 102. Humidity sensor 106E of FIG. 1 shows an example of an inside air humidity sensor 106E. In one or more embodiments, more than one humidity sensor 106A-E may be placed in different locations in the same area, such as an area with a large volume. One or more humidity sensors 106A-D can be placed outside an area to measure outside air humidity (e.g., outdoor air humidity) and transmit an outside air humidity to the thermostat 102. In the embodiment shown in FIG. 1, humidity sensors 106A-D measure outside air humidity and transmit data representative of outside air humidity to the thermostat 102.

Figure 4:
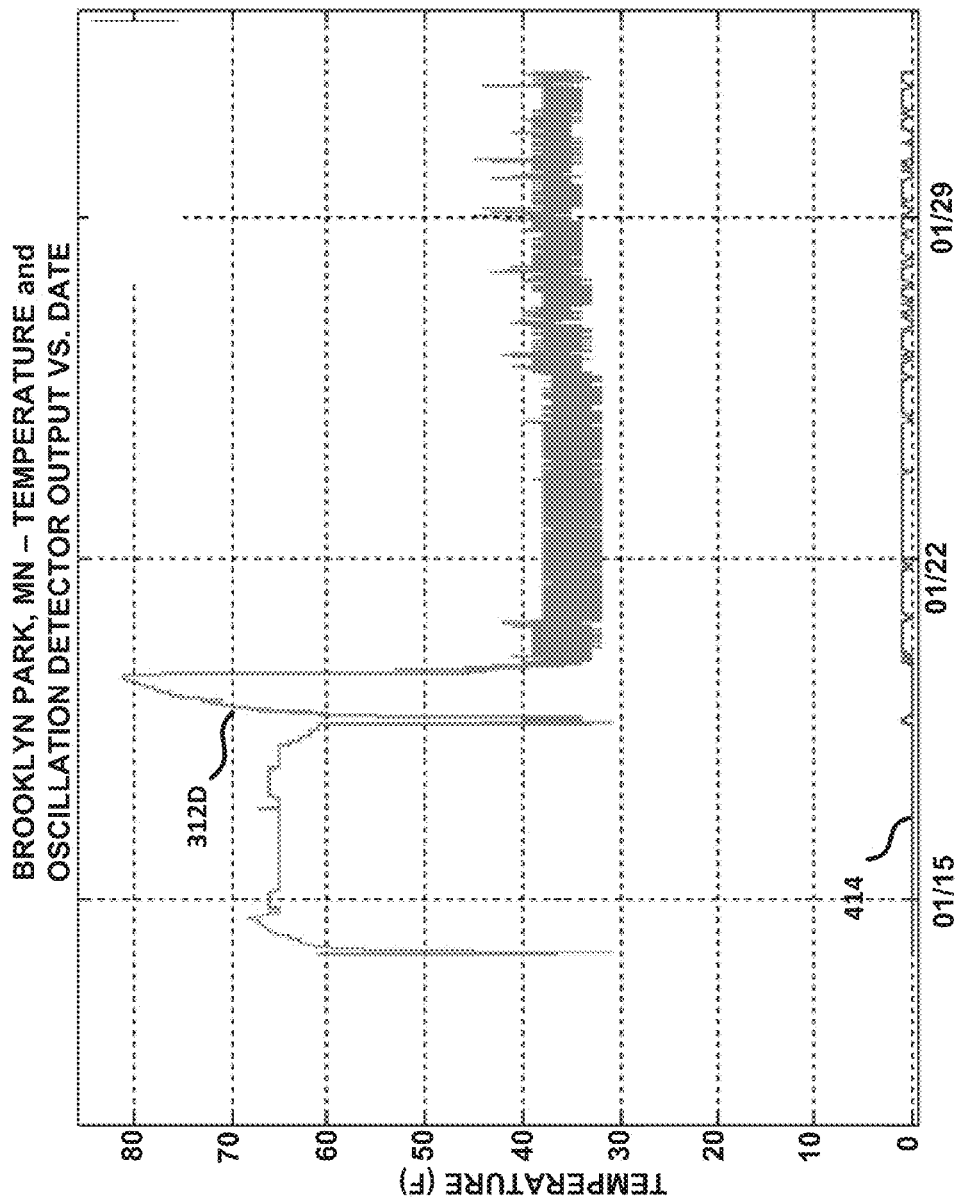
FIG. 4 illustrates an example of a line graph of temperature and a fault detector output versus date for a January in Brooklyn Park, Minn.

Network 110 can be communicatively coupled to the thermostat 102, temperature sensors 104A-E, humidity sensors 106A-E, or computer system(s) 400 (shown in FIG. 4). The network 110 can be configured to relay temperature, humidity, weather forecast (e.g., a predicted temperature, humidity, whether it will rain, snow, or storm, or other weather forecast information) to the thermostat 102.

The network 110, thermostat 102, fault detector 112, computer system 1200 (see FIG. 12), or other device can be configured to detect an anomaly or pattern in the data transmitted by the temperature sensor 104A-E or humidity sensor 106A-E. An anomaly or pattern can be data that is exhibiting behavior consistent with experiencing oscillations, that the data sent from the temperature sensor 104A-E is more consistent with either indoor or outdoor temperatures, or that the temperature sensor 104A-E is sending one, or only a small range, of temperature readings (e.g., a constant minimum or maximum value, or only a small range of temperatures, such as five degrees or less) to the thermostat 102, network 110, or fault detector 112.

Detecting an anomaly in the temperature sensor 104A-E can include determining if the temperature sensor 104A-E is missing or incorrectly installed. Detecting such an anomaly can include determining if the temperature sensor 104A-E is stuck at a specific value or not sending temperature data. An incorrectly installed or missing temperature sensor 104A-E can either send no data or send data that is of a nearly constant value, such as a maximum or a minimum value for the given number of bits, such as −128 F or 128 F. The algorithm can detect such an anomaly by determining if the maximum, minimum, or no value is being transmitted by the temperature sensor 104A-E, such for a specified period of time.

Detecting an anomaly in the temperature sensor 104A-E can include detecting oscillations (e.g., high frequency oscillations or oscillations with a frequency greater than a specified threshold), such as oscillations around a mean value. As used herein, a temperature sensor 104A-E oscillating means that the temperature sensor 104A-E is transmitting data that indicates that the temperature sensor is exhibiting behavior consistent with experiencing oscillations and inconsistent with the normal oscillation patterns of the temperature or humidity readings in the given area around the temperature sensor. Detecting oscillations can be based on the nature (e.g., frequency, magnitude, time of day, among others) of the oscillations or excursions (e.g., oscillations or trend reversals) that are normal for the location of the temperature sensor.

Figure 10:
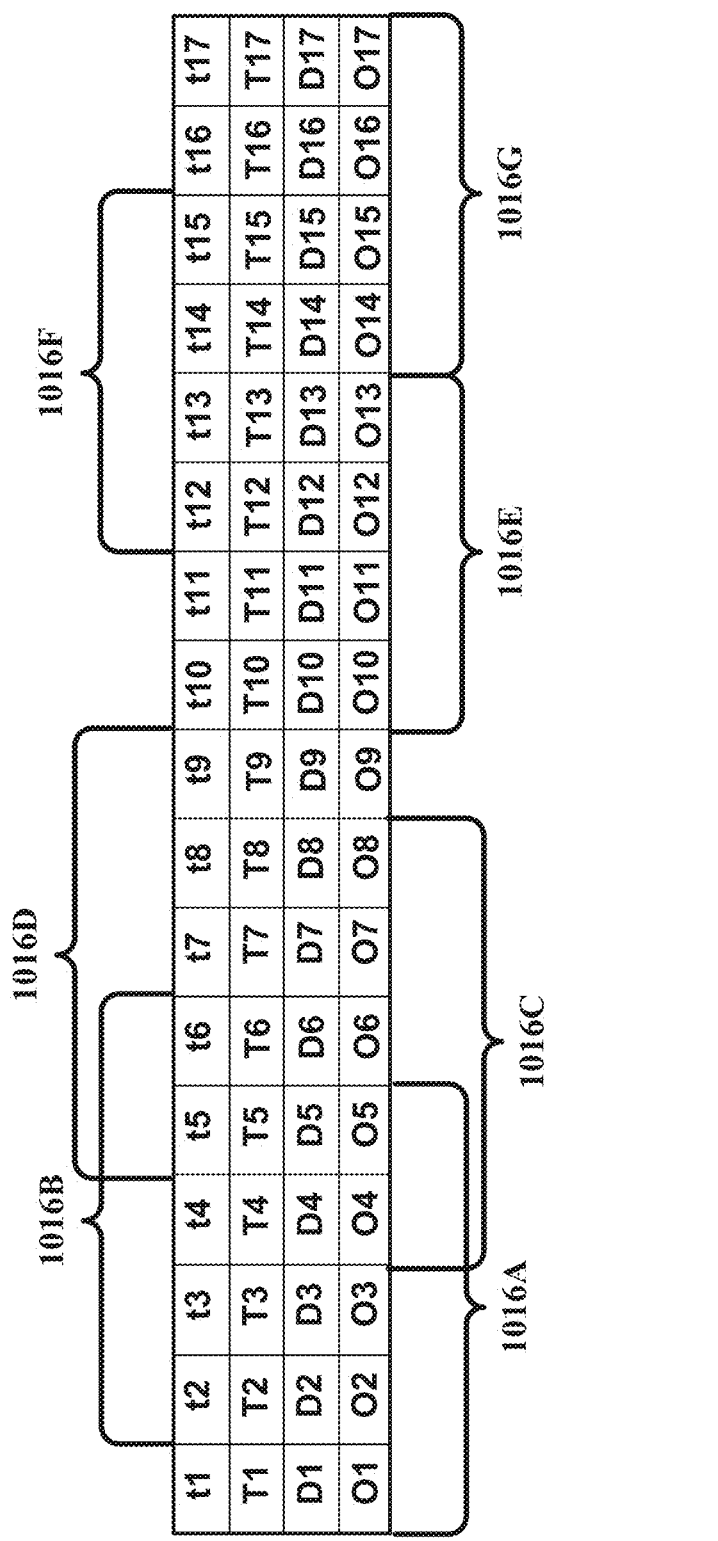
FIG. 10 illustrates a block diagram of examples of time windows and moving or sliding time windows.
Figure 11:
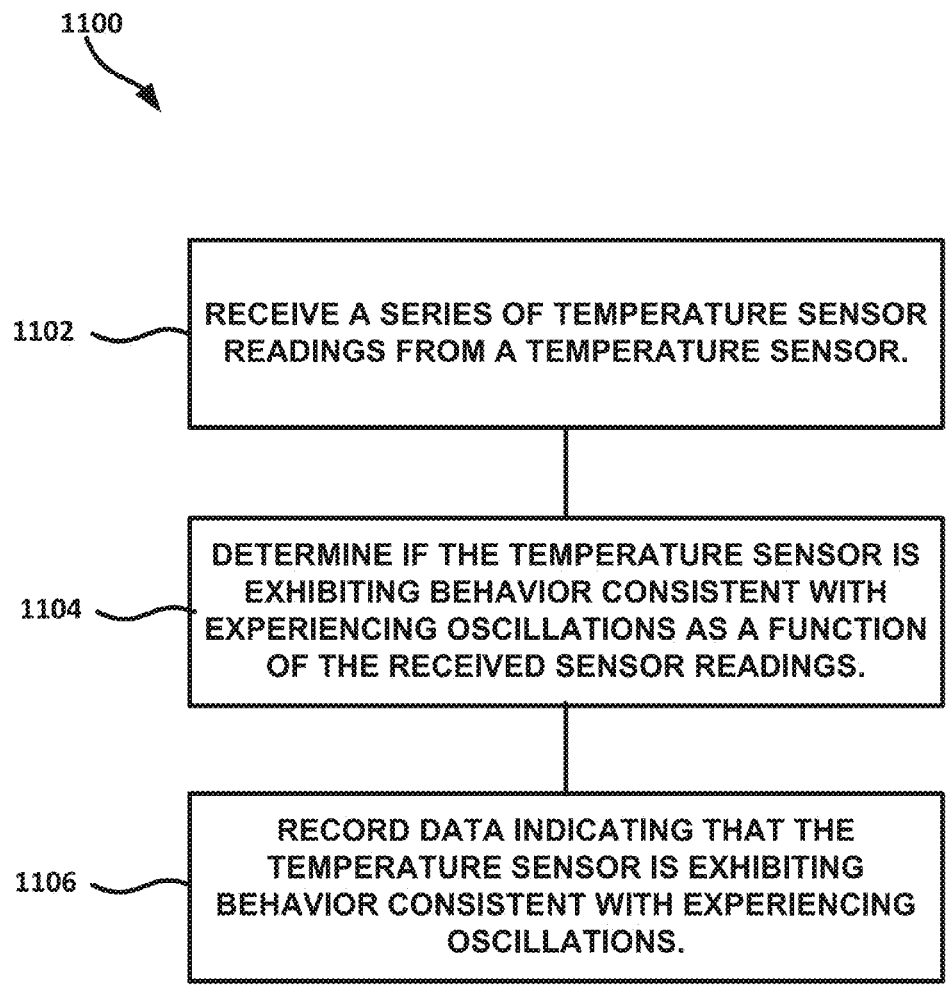
FIG. 11 illustrates a flow diagram of an example of a technique.

Oscillations can be detected by detecting trends (e.g., whether the temperature readings from the temperature sensor 104A-E indicate that the temperature is increasing or decreasing) and updating a trend reversal variable if the temperature goes from increasing to decreasing or decreasing to increasing, such as by counting or incrementing the number of trend reversals within a time window (e.g., a specified or moving time window, see FIG. 10 and the corresponding description of FIG. 10 for more details regarding moving or sliding windows). The trend reversal variable can be compared to previous values of the trend reversal variable detected within a time window of the same size, such as at previous times. Such a comparison can be done to determine if the trend reversals (e.g., oscillations) within the time window is sufficiently close to a specified value (e.g., the number of trend reversals is within one, two, or other number of the expected value for the specified time covered by the time window) so as to determine whether the temperature sensor 104A-E is experiencing an abnormal number of trend reversals within the time window. In one or more embodiments, the comparison can be done to determine if the trend reversal variable remains nearly constant (e.g., the number of trend reversals is within one or two of an expected value). If it is determined that the trend reversal variable is not sufficiently close to the constant value, it can be determined that the temperature sensor is oscillating. If it is determined that an abnormal number of trend reversals has occurred within the time window a fault (e.g., an oscillation fault) can be declared for that time window.

The calculation can be repeated for future time windows. If a fault is declared for a number of sequential time windows (e.g., if a number of sequential faults is determined to be greater than a specified threshold) then it can be determined that the temperature sensor 104A-E is oscillating. In one or more embodiments, detecting if the temperature sensor 104A-E is oscillating can include determining a difference between (1) an average of a minimum and a maximum temperature reading observed in a time window and (2) an average of all temperature readings, such as all temperature readings in the same time window. The difference of averages can be compared to a threshold to determine if it is within an expected range of differences. If the difference of averages is greater than the threshold, then it the oscillations can be determined to be normal oscillations. If the difference of averages is less than the threshold, then the trend reversal variable can be compared to another threshold. In one or more embodiments, an oscillation fault is declared in response to determining that the trend reversal variable is greater than a first threshold and the difference of averages is less than a second threshold.

By detecting oscillations in these ways, false positives can be reduced or even minimized, such as when there are rapid fluctuations in temperature or electronic noise in the sensor data. A threshold value for the trend reversal variable can be assigned based on actual historic sensor data or other sets of normal data. The sequential number of windows with a positive oscillatory behavior (e.g., a fault being declared) can be counted. This sequential number of windows with a positive oscillatory behavior can be compared to a specified threshold that indicates the number of sequential windows to be detected prior to declaring a positive anomaly declaration. Such an approach can help detect anomalous oscillatory behavior correctly or reject declaring a fault when normal sensor oscillations are observed.

Figure 2:
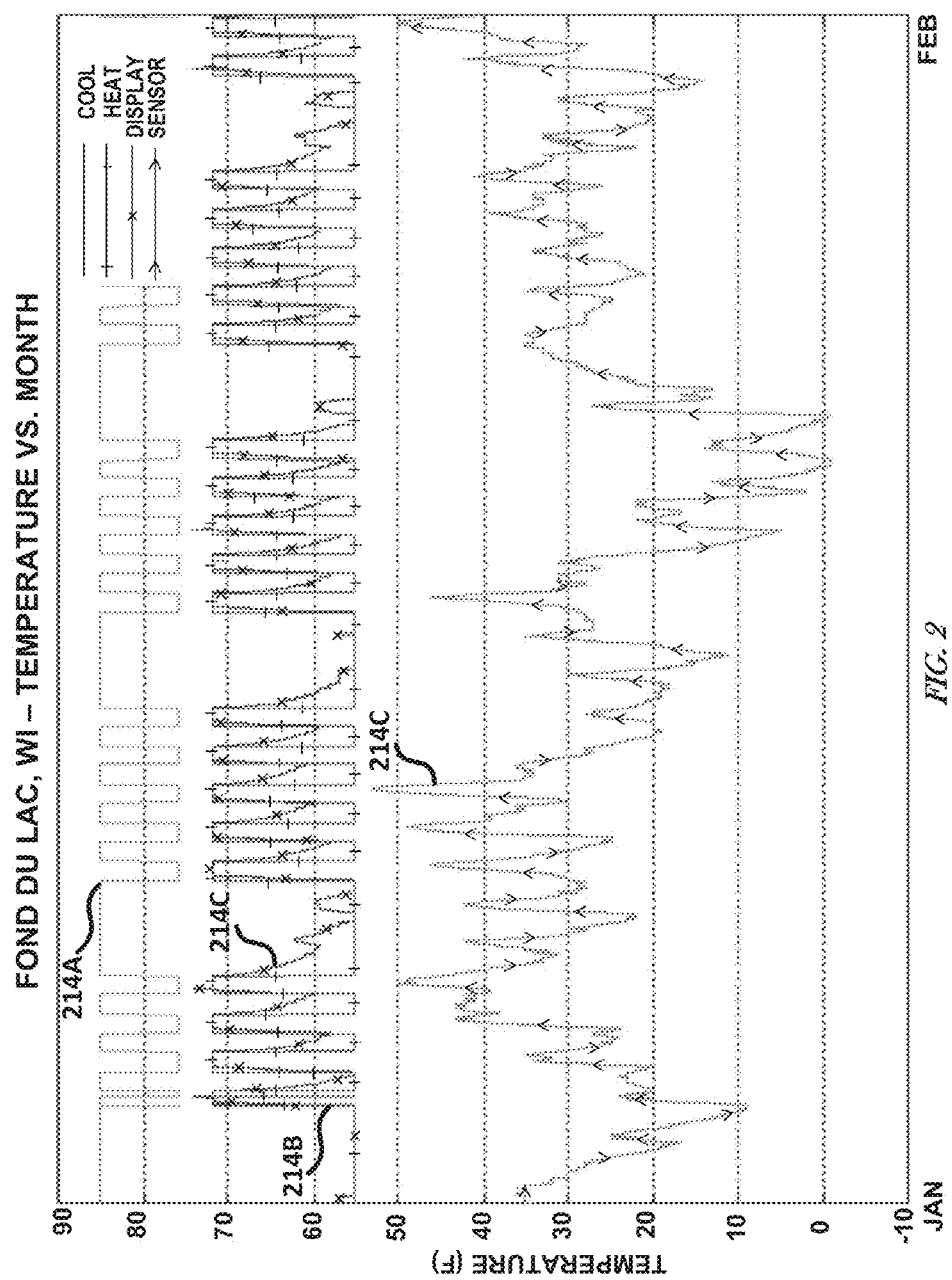
FIG. 2 illustrates an example of a line graph of temperature versus month for a January in Fond Du Lac, Wis.

FIG. 2 shows an example of a line graph of temperature vs. month data for a January in Fond Du Lac, Wis. FIG. 2 shows the cooling set point 214A of a thermostat 102, the heating set point 214B of the thermostat 102, the display temperature 214C on the thermostat 102 display (914A or 914B of FIG. 9, for example), and the sensor temperature 214D from a temperature sensor 104A-E coupled to the thermostat 102 or network 110. The graph in FIG. 2 depicts a normal set of temperature data that is consistent with a temperature sensor 104A-E being located outside in Wisconsin in January and not oscillating, improperly installed, or stuck. This graph can be seen as a control graph depicting normal, expected data or observations.

Figure 3:
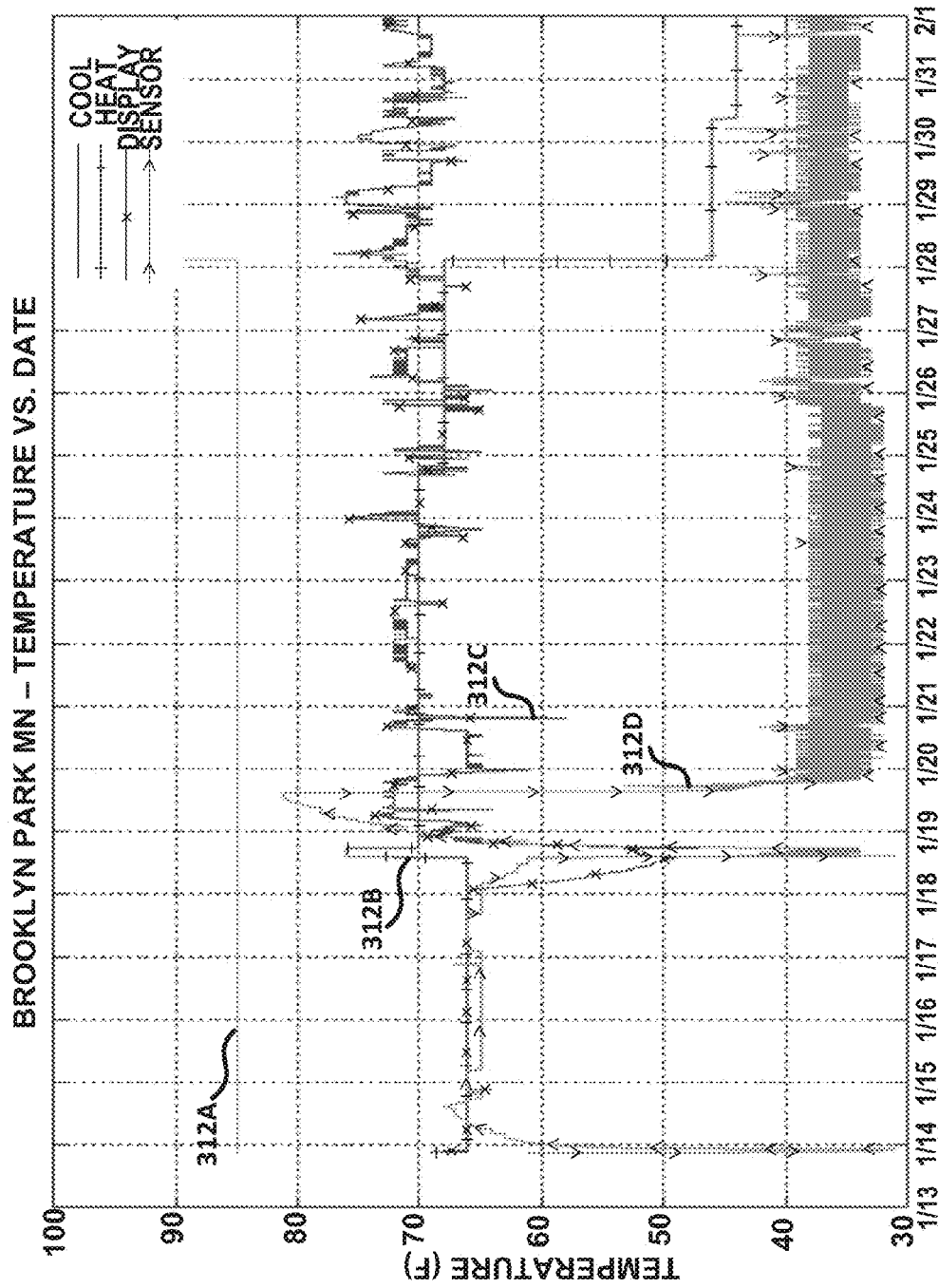
FIG. 3 illustrates an example of a line graph of temperature versus date for a January in Brooklyn Park, Minn.

FIG. 3 shows an example of a line graph of temperature vs. date data for a January in Brooklyn Park, Minn. FIG. 3 shows the cooling set point 312A of a thermostat 102, the heating set point 312B of the thermostat 102, the display temperature 312C on the thermostat 102 display (914A or 914B of FIG. 9, for example), and the sensor temperature 312D from a temperature sensor 104A-E coupled to the thermostat 102 or network 110. As can be seen in FIG. 3, the temperature sensor 104A-E starts oscillating sometime near the end of the day on January 19.

FIG. 4 shows a line graph depicting the sensor temperature 312D from FIG. 3 and the output 414 of the fault detector 112 configured to determine if a temperature sensor 104A-E is oscillating. The output 414 indicates, such as by being asserted to a voltage that corresponds to a binary "1" or being grounded to correspond to a binary "0") that the temperature sensor 104A-E began oscillating at some date between January 15 and January 22, and continued to oscillate beyond January 29. In the embodiment shown in FIG. 4, a fault of the temperature sensor 104A-E is indicated when the output 414 is "1". When the number of faults (e.g., sequential faults) is greater than a specified threshold number of faults, then it can be determined that the temperature sensor 104A-E is oscillating. Proper personnel (e.g., maintenance, a building owner, an employee responsible for ensuring the temperature sensor is in working order, among other personnel) can be alerted in response to determining the temperature sensor 104A-E is oscillating. Such alerts can include a text message, email, sound alarm, or other alert.

Figure 5:
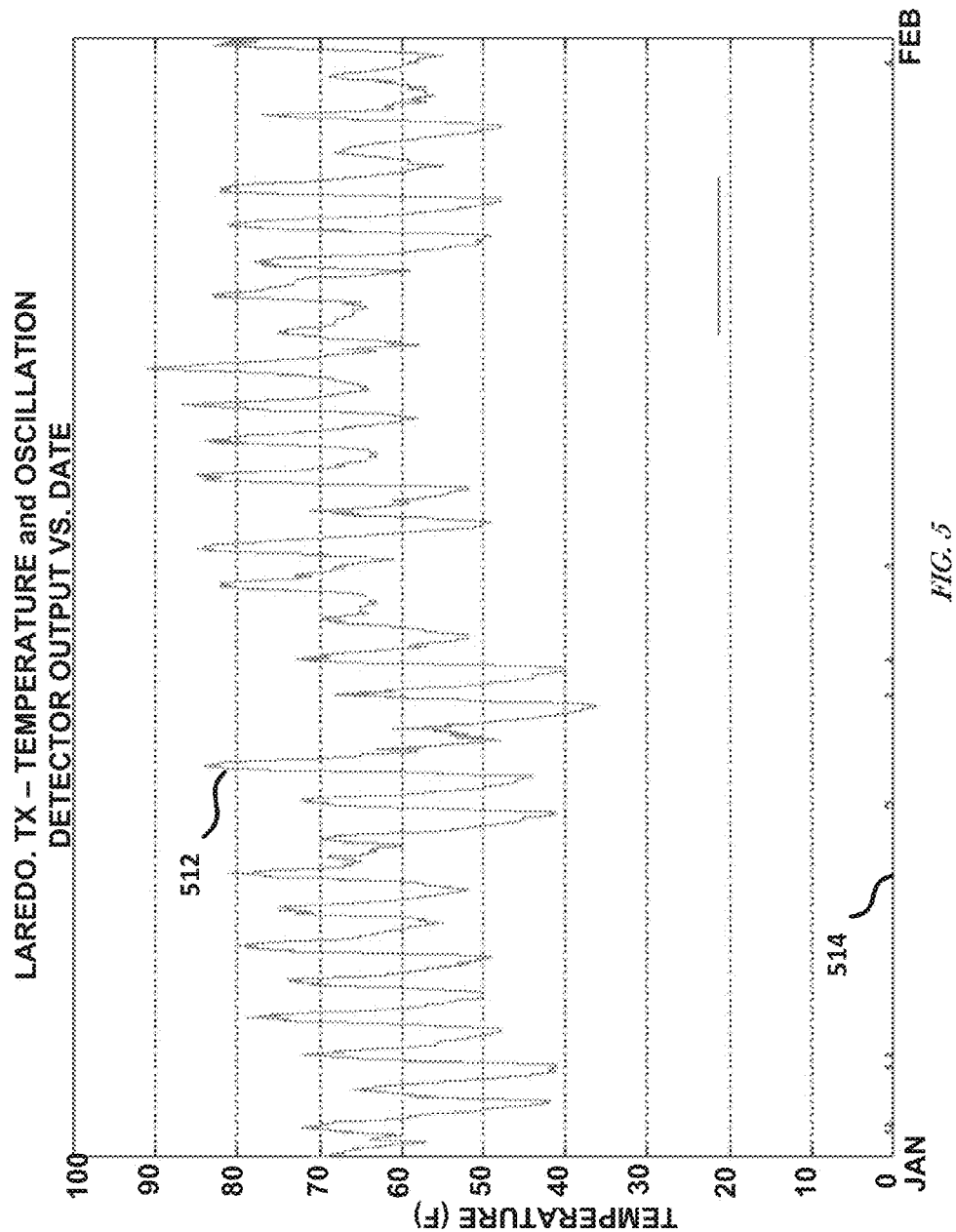
FIG. 5 illustrates an example of a line graph of temperature and a fault detector output versus month for a January in Laredo, Tex.

FIG. 5 shows an example line graph depicting sensor temperature 512 data and a corresponding fault detector 112 output 514 for a January in Laredo, Tex. While some faults are triggered, as indicated by the output 514 being a "1", the temperature sensor 104A-E may not be determined to be oscillating if the threshold number of faults (e.g., sequential faults) is set to a sufficiently high number so as to avoid a single fault triggering a determination that the temperature sensor 104A-E is oscillating. Note that, in FIGS. 4 and 5 the output 414 and 514 indicate if a fault has occurred, where a fault is a preliminary indication that the temperature sensor 104A-E might be oscillating.

Detecting an anomaly in the temperature sensor 104A-E can include determining if the temperature sensor 104A-E is in the proper location (e.g., outdoors or indoors). Such anomalies can be detected based on an outdoor air temperature obtained from an outside source, such as a website (e.g., Weather Underground, weather.com, or other website that maintains such data). The data collected from the temperature sensor 104A-E and the outside source can be divided into respective time windows. In one or more embodiments, it can be determined if a display temperature is sufficiently different from the outdoor temperature (e.g., about five degrees F. different or more). Such a determination can help ensure that a sufficient difference between the indoor and outdoor temperatures exists so as to be gable to determine if the temperature sensor readings are more closely correlated with one of them and not the other. Having indoor and outdoor temperatures that are close to each other can cause difficulties in determining which of the indoor or outdoor temperatures the sensor temperature is more closely correlated with.

Differences can be calculated as: (1) the temperature obtained from the outside source minus the temperature detected by the temperature sensor 104A-E and (2) a temperature set point of the corresponding thermostat and the temperature detected by the temperature sensor. The differences calculated can be used to determine Root Mean Square (RMS) errors between the temperature detected by the temperature sensor and the outdoor and indoor temperatures, respectively. The differences can be calculated as a function of each temperature reading received from the temperature sensor within a time window (e.g., a moving or sliding time window). Such calculations can help determine if the outdoor temperature sensed a temperature closer to the outdoor temperature indicated by the outside source or the room/zone temperature indoors.

A threshold can be specified so as to set a limit on a ratio between the differences or errors calculated based on the differences: (1) the temperature obtained from the outside source minus the temperature detected by the temperature sensor and (2) a temperature set point of the corresponding thermostat minus the temperature detected by the temperature sensor 104A-E. If the ratio between the errors or differences is greater than the threshold, a fault can be triggered. If a specified number of sequential faults is triggered (e.g., if a number of sequential faults exceeds a threshold) a location of the temperature sensor 104A-E can be determined to be in error (e.g., a location fault for the temperature sensor 104A-E can be declared). Such an approach can help detect anomalies where the temperature sensor is not properly located and can help reduce the number of false positives declared as compared to using other algorithms to detect the same.

Figure 6:
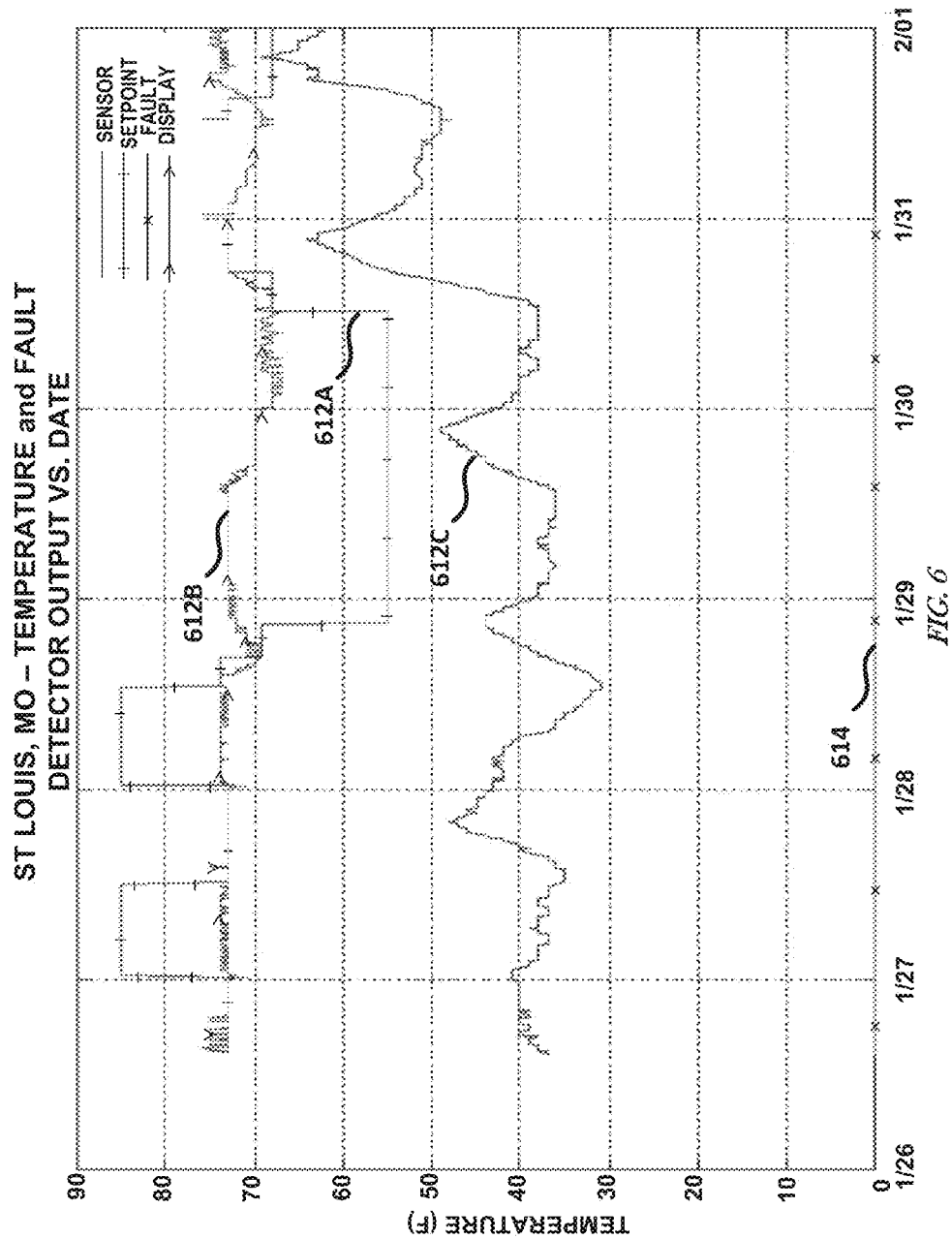
FIG. 6 illustrates an example of a line graph of temperature and a fault detector output versus date for a January in Saint Louis, Mo.

FIG. 6 shows an example of a line graph of temperature and fault detector 112 output versus date for a January in Saint Louis, Mo. The line graph includes set point temperature 612A, thermostat 102 display temperature 612B, sensor temperature 612C and fault detector 112 output 614. The fault detector 112 in this embodiment is determining if the temperature sensor 104A-E is properly located. In this embodiment the temperature sensor 104A-E is supposed to be located outdoors. The sensor temperature 612C detected by the temperature sensor 104A-E should have little or no correlation with the indoor or display temperature 612B. If it is determined that the sensor temperature 612C and the display temperature 612B are sufficiently correlated (e.g., if a ratio between differences or errors calculated based on the differences: (1) the temperature obtained from the outside source minus the temperature detected by the temperature sensor 104A-E and (2) a temperature detected by the corresponding thermostat minus the temperature detected by the temperature sensor 104A-E, is greater than a specified threshold) then a fault can be declared (e.g., the output 614 of the fault detector 112 can be asserted or grounded, as appropriate). As can be seen in FIG. 6, though, no faults have been declared since the display temperature 612B and the sensor temperature 612C are not sufficiently correlated in this example.

Figure 7:
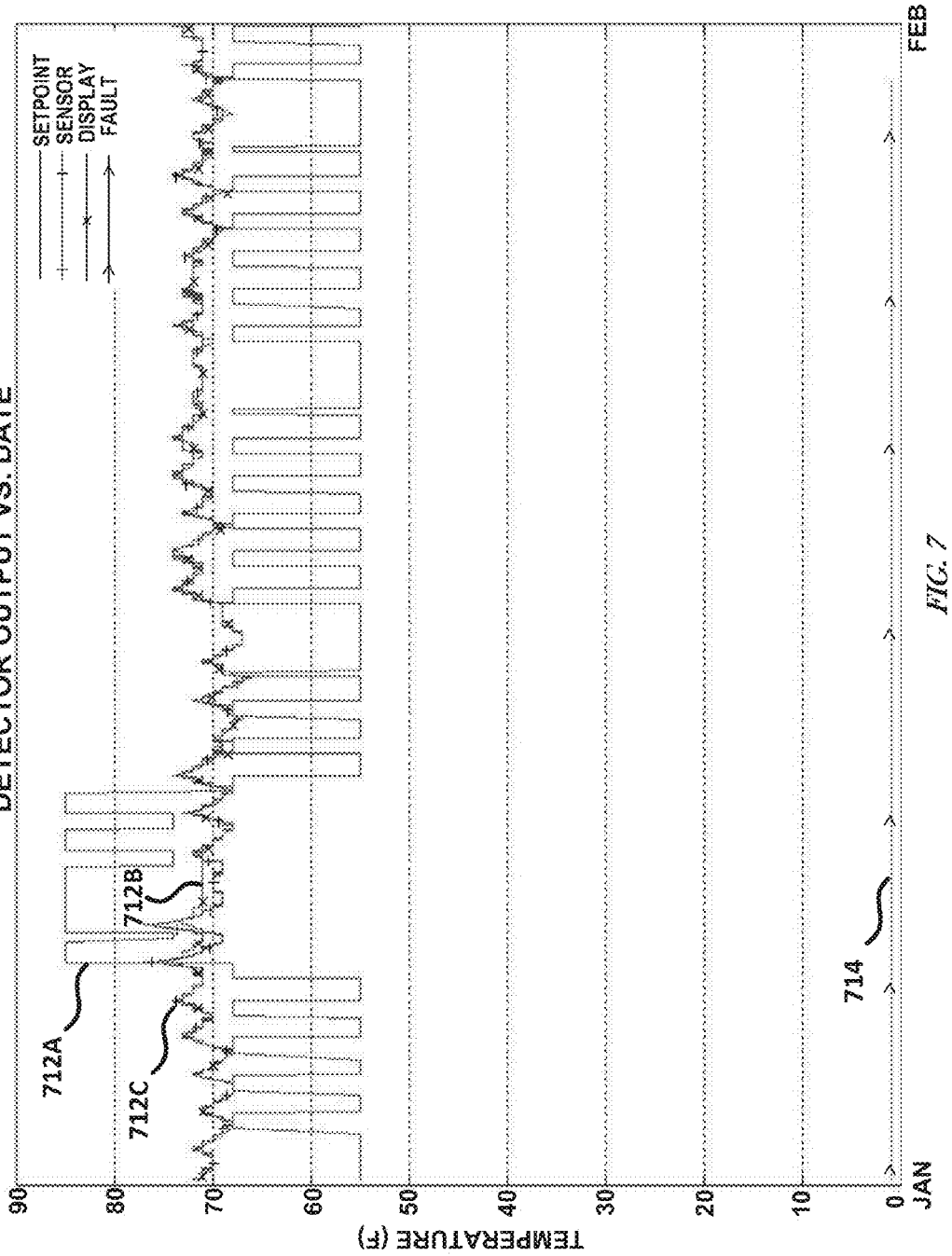
FIG. 7 illustrates an example of a line graph of temperature and a fault detector output versus month for January in San Antonio, Tex.

FIG. 7 shows an example of a line graph of temperature and fault detector 112 output versus month for a January in San Antonio, Tex. The line graph includes set point temperature 712A, thermostat 102 display temperature 712B, sensor temperature 712C, and fault detector 112 output 714. In this example the temperature sensor 104A-E is supposed to be located outdoors. As can be seen in FIG. 7, there is a strong correlation between the sensor temperature 712C and the display temperature 712B. The fault detector 112 output 714 in this example is constantly asserted at "1" since the ratio of differences or errors (as discussed in the previous paragraph) is greater than a specified threshold. In this case, since the sensor temperature 712C and the display temperature 712B are so closely correlated, the difference between sensor temperature 712C and the display temperature 712B (and a corresponding error calculated based on these values) would be small relative to the example shown in FIG. 6. Thus, the number that is the ratio of differences or errors would be relatively large (e.g., because the denominator of the ratio is small).

Figure 8:
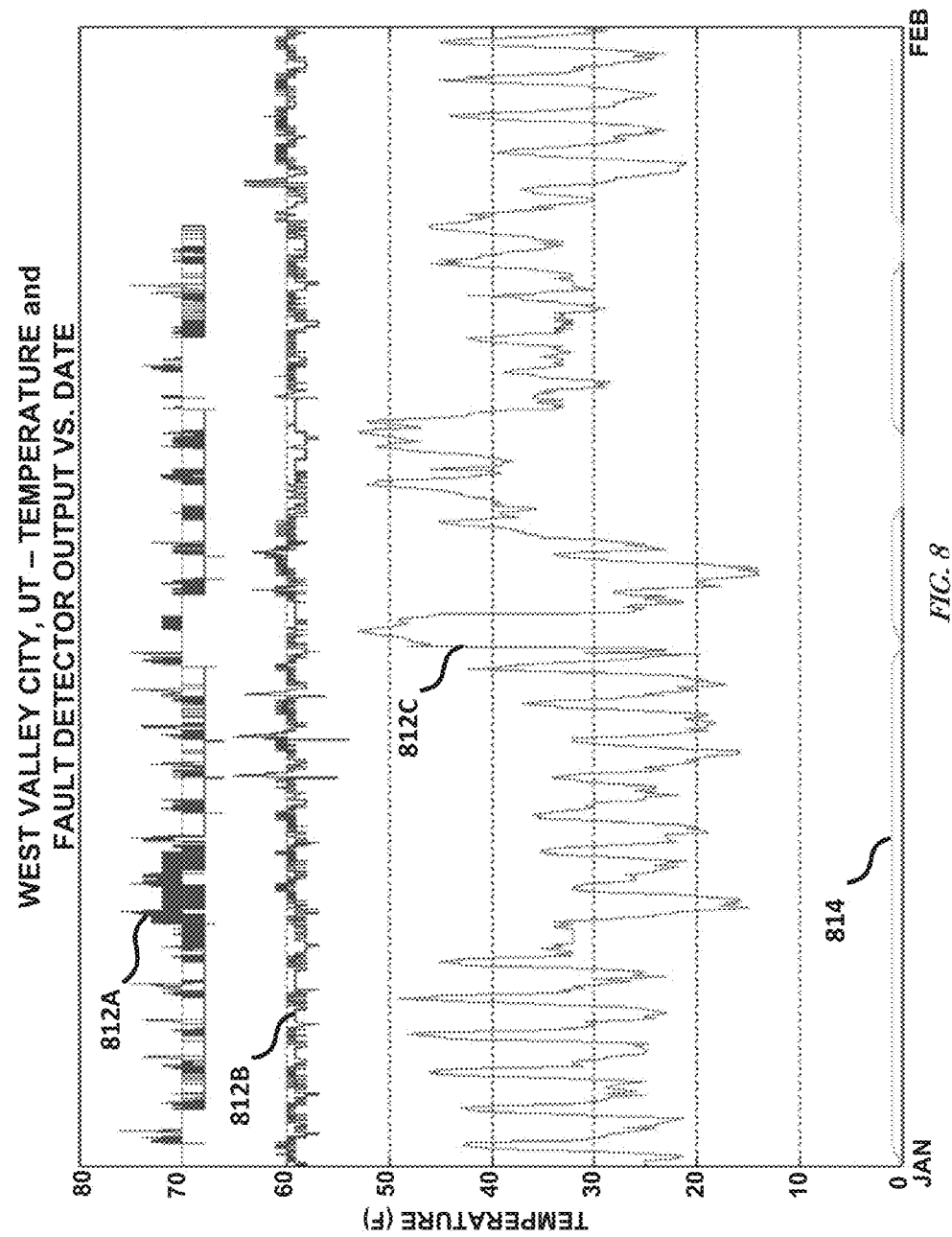
FIG. 8 illustrates an example of a line graph of temperature and a fault detector output versus month for January in West Valley City, Utah.

FIG. 8 shows an example of a line graph of temperature and fault detector 112 output versus month for a January in West Valley City, Utah. The line graph includes thermostat 102 display temperature 812A, sensor temperature 812B, outdoor temperature data 812C received from an outside source and fault detector 112 output 814. In this example, the temperature sensor 104A-E is supposed to be located outdoors. As can be seen, the fault detector 112 output 814 indicates that the temperature sensor 104A-E is likely located improperly. This is because the fault detector 112 output 814 is asserted for a majority of the time, or because a number of faults (e.g., sequential faults) meets or exceeds a specified threshold. In this example, the temperature sensor 104A-D could be located outdoors, but in a location that is warmer than normal outdoor temperatures in the region. As a result, the temperature sensor 104A-D is not getting an accurate reading of the outdoor temperature.

The fault detector 112 output 814 being asserted can indicate that the sensor temperature is too closely correlated or not sufficiently correlated to (1) the outdoor temperature data 812C or (2) the display temperature 812A. By configuring which error or difference is in the numerator or denominator of the ratio and modifying the threshold, the system, apparatus, or technique can be configured to detect whether the is too closely correlated or not sufficiently correlated to (1) the outdoor temperature data 812C or (2) the display temperature 812A. For example, to determine if the sensor temperature 812B is sufficiently correlated to the indoor temperature the ratio can be configured to have the difference or error calculated based on (1) the temperature obtained from the outside source minus the temperature detected by the temperature sensor in the denominator and (2) a temperature detected by an indoor temperature sensor 104A-E communicating with the thermostat 102 minus the temperature detected by the temperature sensor 104A-E in the numerator. If this ratio is greater than a specified threshold, then the sensor temperature readings can be determined to be not sufficiently correlated to the indoor temperature (e.g., display temperature 812A) and a fault can be declared.

Figure 9:
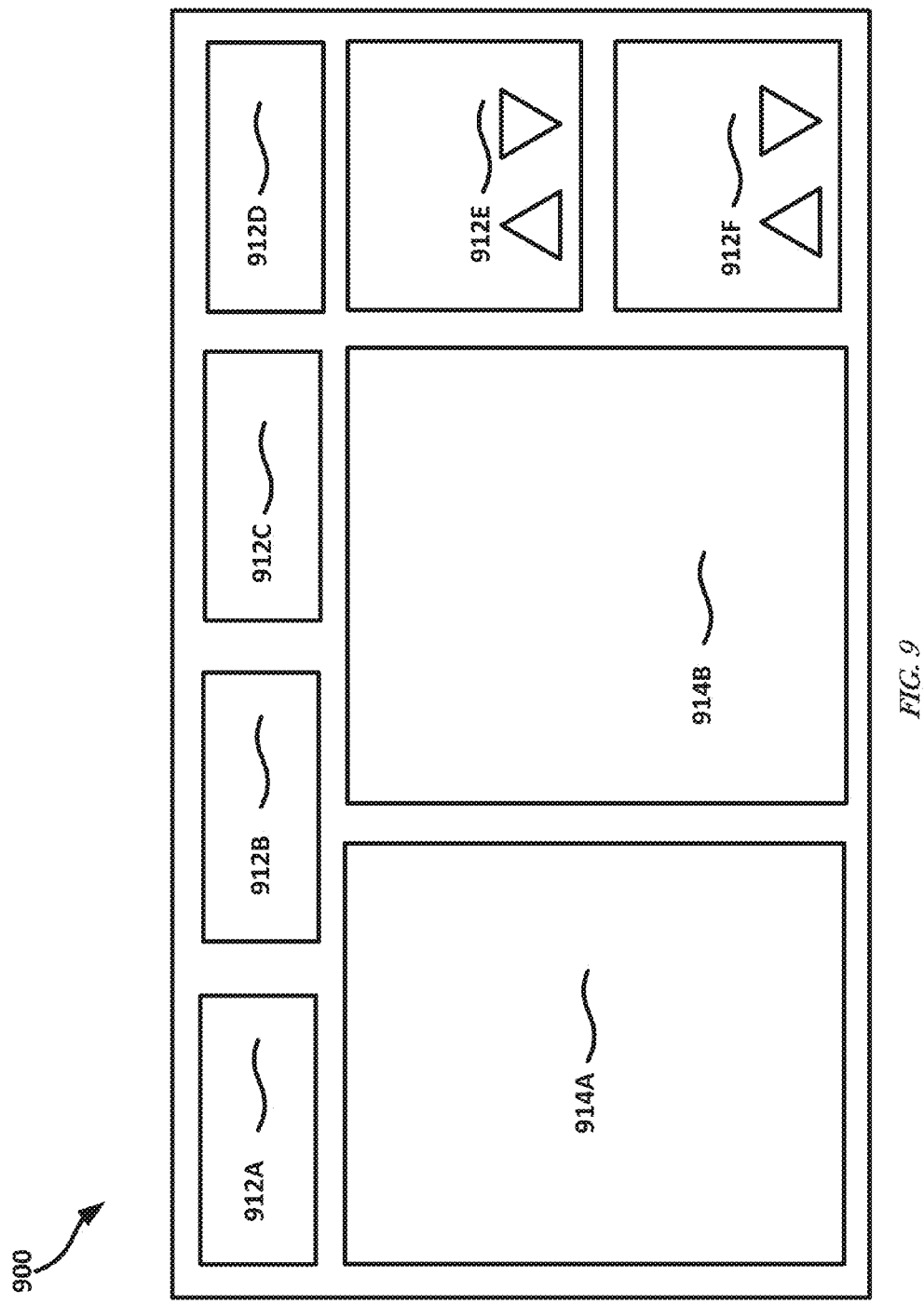
FIG. 9 illustrates a block diagram of an example of a user-interface of a thermostat.

FIG. 9 shows an example of a user interface 900 of a thermostat 102. The user interface 900 can include one or more settings buttons 912A-F and one or more information screens 914A-B. The settings buttons 912 can correspond to configuring what is displayed on the information screens 914, heating or cooling settings, system information and configuration options, or ventilation options, among others. For example, a user can configure the temperature set points of the thermostat 102 using the heating or cooling settings. In one or more embodiments, a user can set a temperature set point that indicates when the thermostat 102 should initiate heating an area and another temperature set point that indicates when the thermostat 102 should initiate cooling an area, such as by using the up and down arrows of settings buttons 912E and 912F, respectively. The thermostat 102 may include a limited user interface, or no user interface and be controlled remotely via an application, such as a Smartphone application.

The user can set a temperature schedule through the user interface 900. The user can enter information about the area the thermostat 102 is responsible for through the user interface 900. For example, the user can enter data about the insulation used in the area, a square footage of the area, a website that the network 110 can pull weather data from, a zip code or other information indicating a geographical location of the area, or other area information through the user interface 900.

The information screen(s) 914 can display a temperature received from a temperature sensor 104A-E, a humidity received from a humidity sensor 106A-E, an indoor or outdoor temperature, a weather forecast, the temperature set point(s), or other system information.

FIG. 10 shows an example of time series data (sensor temperature readings "T1", "T2", . . . and "T17", display temperatures "D1", "D2", . . . and "D17, and outdoor temperatures "O1", "O2", . . . and "O17", corresponding to (e.g., received at) times "t1", "t2", . . . , "t17", respectively) received from a temperature sensor 104A-E, the network, or other source and illustrates a plurality of example time windows 1016A, 1016B, 1016C, 1016D, 1016E, 1016F, and 1016G.

Time window 1016A is configured for five time units, t1 through t5 in this example. The sensor temperatures, T1 through T5, from the respective temperature sensor 104A-E, the display temperatures D1 through D5, or the outdoor temperatures O1 through O5 can be used to determine if a fault should be declared in the time window 1016A. After time t6 has passed and the corresponding temperatures T6, D6, and O6 have been determined or received from their respective components or the network 110, time window 1016A can slide a time unit to become time window 1016B. The sensor temperatures, T2 through T6, display temperatures D2 through D6, or the outdoor temperatures O2 through O6 can be used to determine if a fault should be declared in the time window 1016B. In this example, time window 1016A and 1016B are sequential time windows. Note that a time window can slide more than one time unit before the data in the time window 1016A-G is used to determine if a fault should be declared. For example, time window 1016C can be a time window that is sequential with time window 1016A but is delayed three time units from time window 1016A (e.g., from beginning at time t1 to beginning at time t4). The size (e.g., time span or duration) of the time windows 1016A-G can vary as well. Time windows 1016E, 1016F, and 1016G are depicted as spanning four time units, while time windows 1016A, 1016B, 1016C, and 1016D are depicted as spanning five time units. It should be appreciated that time windows with other sizes can be used and are still consistent with this disclosure. Note that time units can be any duration from fractions of a second to days, weeks, or even months apart.

Time window 1016F can be two time units moved from time window 1016E and sequential (e.g., the next time window in a sequence) with time window 1016E. Time window 1016G can be two time units moved or slid down from time window 1016F and sequential with time window 1016F. In one or more embodiments, a location or oscillation fault can be declared for if specific criteria are met within a single time window 1016A-G, but an alert or other declaration that the temperature is oscillating or in an improper location can be declared if the data in a specified number (e.g., a threshold number) of sequential time windows meets or exceeds the criteria. The threshold can be any number, one or more. In this way, a tolerance for some oscillations or correlation issues between the sensor temperature and either the indoor or outdoor temperatures can be tolerated without triggering an alert.

Figure 12:
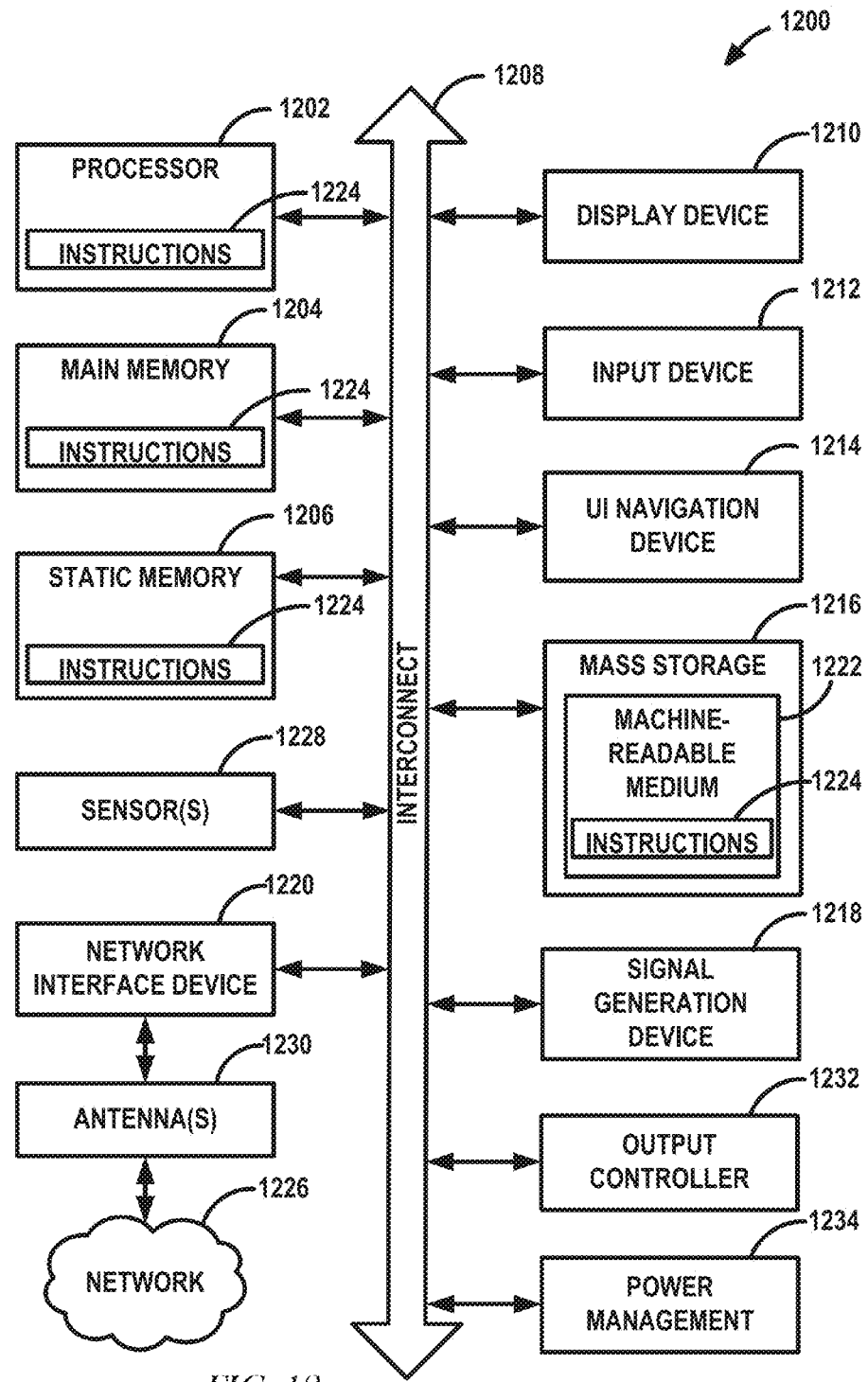
FIG. 12 illustrates a block diagram of an example of a computer system.

FIG. 12 is a block diagram illustrating an example computer system machine upon which any one or more of the techniques herein discussed may be run, such as a computer system 1200 that can be communicatively coupled to a thermostat 102, network 110, or fault detector 112. In one or more embodiments, thermostat 102, network 110, or fault detector 112 can include one or more items of computer system 1200. Computer system 1200 may be embodied as a computing device, providing operations of a thermostat 102 (from FIG. 1), network, or fault detector 112 or any other processing or computing platform or component described or referred to herein. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The computer system machine may be a personal computer (PC), such as a PC that can be portable (e.g., a notebook or a netbook) or a PC that is not conveniently portable (e.g., a desktop PC), a tablet, a set-top box (STB), a gaming console, a Personal Digital Assistant (PDA), a mobile telephone or Smartphone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Implementing techniques using computer processors and other logic can lead to automated anomaly detection (e.g., anomaly or fault detection that does not include human interference). Recommendations for operator, owner, or other personnel action for energy saving measures or maintenance suggestions can be provided (e.g., automatically) using techniques detailed herein.

Example computer system 1200 can include a processor 1202 (e.g., a central processing unit (CPU), a graphics processing unit (GPU) or both), a main memory 1204 and a static memory 1206, which communicate with each other via an interconnect 1208 (e.g., a link, a bus, etc.). The computer system 1200 may further include a video display unit 1210, an alphanumeric input device 1212 (e.g., a keyboard), and a user interface (UI) navigation device 1214 (e.g., a mouse). In one embodiment, the video display unit 1210, input device 1212 and UI navigation device 1214 are a touch screen display. The computer system 1200 may additionally include a storage device 1216 (e.g., a drive unit), a signal generation device 1218 (e.g., a speaker), an output controller 1232, a power management controller 1234, and a network interface device 1220 (which may include or operably communicate with one or more antennas 1230, transceivers, or other wireless communications hardware), and one or more sensors 1228, such as a GPS sensor, compass, location sensor, accelerometer, or other sensor.

The storage device 1216 includes a machine-readable medium 1222 on which is stored one or more sets of data structures and instructions 1224 (e.g., software) embodying or utilized by any one or more of the methodologies or functions described herein. The instructions 1224 may also reside, completely or at least partially, within the main memory 1204, static memory 1206, and/or within the processor 1202 during execution thereof by the computer system 1200, with the main memory 1204, static memory 1206, and the processor 1202 also constituting machine-readable media.

While the machine-readable medium 1222 is illustrated in an example embodiment to be a single medium, the term "machine-readable medium" may include a single medium or multiple media (e.g., a centralized or distributed database, and/or associated caches and servers) that store the one or more instructions 1224. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, optical media, and magnetic media. Specific examples of machine-readable media include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 1224 may further be transmitted or received over a communications network 1226 using a transmission medium via the network interface device 1220 utilizing any one of a number of well-known transfer protocols (e.g., HTTP). Examples of communication networks include a local area network (LAN), wide area network (WAN), the Internet, mobile telephone networks, Plain Old Telephone (POTS) networks, and wireless data networks (e.g., Wi-Fi, 3G, and 4G LTE/LTE-A or WiMAX networks). The term "transmission medium" shall be taken to include any intangible medium that is capable of storing, encoding, or carrying instructions for execution by the machine, and includes digital or analog communications signals or other intangible medium to facilitate communication of such software.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in this document, the terms "first," "second," and "third," etc. are used merely as labels, and are not intended to impose numerical requirements on their objects.

As used herein, a "-" (dash) used when referring to a reference number means or, in the non-exclusive sense discussed in the previous paragraph, of all elements within the range indicated by the dash. For example, 103A-B means a nonexclusive or of the elements in the range {103A, 103B}, such that 103A-103B includes "103A but not 103B", "103B but not 103A", and "103A and 103B".

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

The invention claimed is:

1. A system comprising:
   one or more temperature sensors;
   one or more memories;
   internet-coupled thermostats including one or more computer processors, the one or more computer processors coupled to the one or more temperature sensors and the one or more memories, the one or more computer processors configured to:
      receive a series of temperature sensor readings from the temperature sensor;
      determine if the temperature sensor is experiencing oscillations as a function of the received sensor readings, including:
      determine if the received sensor readings indicate that the temperature at the temperature sensor is increasing or decreasing,
      update a trend reversal variable in response to determining the received sensor readings indicate a temperature went from increasing to decreasing or decreasing to increasing,
      determine a difference between an average of a maximum and a minimum of the temperature sensor readings in a moving time window and an average of all temperature sensor readings in the time window,
      determine if the difference is less than a first specified threshold,
      determine if the trend reversal variable is greater than a second threshold, and
      determine the temperature sensor is experiencing oscillations in response to determining at least one of: the difference is less than the first threshold and the trend reversal variable is greater than the second threshold; and
   in response to determining that the temperature sensor is experiencing oscillations, recording, in the memory, data indicating that the temperature sensor is experiencing oscillations; and a display coupled to the one or more computer processors to alert personnel that the temperature sensor is experiencing oscillations in response to determining the temperature sensor is experiencing oscillations.

2. The apparatus of claim 1, wherein the trend reversal variable indicates how many trend reversals occurred in the moving time window.

3. A method comprising:

receiving, at a computer processor of an internet-connected thermostat and from a temperature sensor communicatively coupled to the internet-connected thermostat, a series of temperature sensor readings from a temperature sensor;

determining, using the computer processor, if the temperature sensor is experiencing oscillations as a function of the received sensor readings;

determining if the received sensor readings indicate that the temperature at the temperature sensor is increasing or decreasing, updating a trend reversal variable in response to determining the received sensor readings indicate a temperature went from increasing to decreasing or decreasing to increasing, determining a difference between an average of a maximum and a minimum of the temperature sensor readings in a moving time window and an average of all temperature sensor readings in the time window, determining if the difference is less than a first specified threshold, determining if the trend reversal variable is greater than a second threshold, and determine the temperature sensor is experiencing oscillations in response to determining at least one of: the difference is less than the first threshold and the trend reversal variable is greater than the second threshold;

in response to determining that the temperature sensor is experiencing oscillations, recording in a memory communicatively coupled to the computer processor data indicating that the temperature sensor is experiencing oscillations; and alerting personnel, using at least one of a display and a speaker coupled to the computer processor, that the temperature sensor is experiencing oscillations in response to determining the temperature sensor is experiencing oscillations.

4. The method of claim 3, wherein the trend reversal variable indicates how many trend reversals occurred in the moving time window.

5. A computer readable storage device of an internet-connected thermostat comprising instructions stored thereon, the instructions, which when executed by a computer processor of the internet-connected thermostat, cause the computer processor to perform operations comprising:

receiving a series of temperature sensor readings from a temperature sensor;

determining if the temperature sensor is exhibiting behavior consistent with experiencing oscillations as a function of the received sensor readings;

determining if the received sensor readings indicate that the temperature at the temperature sensor is increasing or decreasing, updating a trend reversal variable in response to determining the received sensor readings indicate a temperature went from increasing to decreasing or decreasing to increasing, determining a difference between an average of a maximum and a minimum of the temperature sensor readings in a moving time window and an average of all temperature sensor readings in the time window, determining if the difference is less than a first specified threshold, determining if the trend reversal variable is greater than a second threshold, and determine the temperature sensor is experiencing oscillations in response to determining at least one of: the difference is less than the first threshold and the trend reversal variable is greater than the second threshold;

in response to determining that the temperature sensor is experiencing oscillations, recording in a memory coupled to the internet-coupled thermostat, data indicating that the temperature sensor is exhibiting behavior consistent with experiencing oscillations; and providing one or more signals to at least one of a display and a speaker coupled to the computer processor, the signals causing the display or speaker that the temperature sensor is experiencing oscillations in response to determining the temperature sensor is experiencing oscillations.

* * * * *